United States Patent
Gonsalves et al.

(10) Patent No.: US 6,667,062 B2
(45) Date of Patent: Dec. 23, 2003

(54) COMPOSITION COMPRISING ZOANTHUS SP. EXTRACT WITH ANTI-FOULING ACTIVITY AND A METHOD THEREOF

(75) Inventors: Cynthia Olimpia Lydia Gonsalves, Goa (IN); Chittur Thelakkat Achuthankutty, Goa (IN); Perunninakulath Parameswaran Subrayan, Goa (IN); Chandrakant Govind Naik, Goa (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/108,760

(22) Filed: Mar. 27, 2002

(65) Prior Publication Data
US 2003/0185897 A1 Oct. 2, 2003

(51) Int. Cl.[7] ................................................. A61K 35/12
(52) U.S. Cl. ....................................................... 424/520
(58) Field of Search .......................................... 424/520

(56) References Cited

FOREIGN PATENT DOCUMENTS

| EP | 1138690 | * | 4/2001 |
| JP | 406199867 | * | 6/1994 |

* cited by examiner

Primary Examiner—Herbert J. Lilling
(74) Attorney, Agent, or Firm—Merchant & Gould, P.C.

(57) ABSTRACT

The present invention relates to a composition useful as an anti-fouling agent by inhibiting microbial growth, said comprising extract and/or its fractions from Zoanthus sp. and optionally de-odorizing agents and a method of producing said extract and its fractions having about 100% anti-bacterial activity fouling microbes.

15 Claims, No Drawings

COMPOSITION COMPRISING ZOANTHUS SP. EXTRACT WITH ANTI-FOULING ACTIVITY AND A METHOD THEREOF

FIELD OF THE PRESENT INVENTION

The present invention relates to a composition useful as an anti-fouling agent by inhibiting microbial growth, said composition comprising extract and/or its fractions from Zoanthus sp. and optionally de-odorizing agents and a method of producing said extract and its fractions having about 100% anti-bacterial activity fouling microbes.

BACKGROUND AND PRIOR ART REFERENCES

Chemical antifouling defense strategies of marine organisms have been studied either directly against the target fouling organisms such as bacteria, fungi, algae, invertebrate larvae, etc. (Amade et ai., 1987, Mar. Biol. 94, 271–275; Slattery et al., 1995, J. Exp. Mar. Biol. Ecol, 190, 61–77; Shellenberger and Ross, 1998, Northwest Science, 72(1), 23–33) or using other fouling measures like settlement inhibition, larval moulting rates, photosynthesis, etc. (Konya et al., 1994, Fish. Sci, 60(6), 773–775; Kato et al., 1995, Tetrahedron letters, 36(12), 2133–2136; Mizobuchi et al., 1996, Fisheries Sci, 62(1), 98–100; Becerro et al., 1997, J. Chem. Ecol, 23(6), 1527–1547).

Information on secondary metabolite production marine organisms deals mostly with isolation and characterization of the compounds and very little is known about their ecological and biological importance. In recent years, some attempts have been made in this direction on a few groups such as soft corals, gorgonians, algae, sponges, bryozoans, etc. (Targett, 1988, in Marine Biodeterioration, M. F. Thompson., R. Sarojini., R. Nagabhushanam., A A Balkema eds, Rotterdnm, 607–617; Standing et al., 1984, J. Chem. Ecol, 10, 823–824; Davis et al., 1991, Mar. Ecol, Prog. Ser, 72, 117–123; Vitalina et al., 1991, in Bioactive compounds from marine organisms, M. F. Thompson., R. Sarojini., R. Nagabhushanam eds, Oxford and IBH Publishing Co. Pvt. Ltd, 63–68; Szewzyk et al., 1991, Mar. Ecol. Prog. Ser, 75, 259–265) leaving many other groups unstudied. Zoanthid (Phylum Coelenterata; Family Zoanthidae) is one such group which has received very little attention with respect to chemical defense strategies.

Zoanthids are benthic, sessile, colony forming organisms, comprising of thousands of individual polyps. Several chemical compounds have been isolated from zoanthids, possessing various pharmacological properties,(Moore and Scheuer, 1971, Science, 172, 495–498; Cimino et al., 1973,; Sturaro et al., 1982; Rao et al., 1985, J. Org. Chem, 50, 3757–3760; Bakus et al., 1986, J. Chem. Ecol, 12, 951–987; Quinn, 1988, in Bioorganic Marine Chemistry, P. J. Scheuer ed. Vol 2, 25–27; Shigemori et al., 1999, J. Nat. Prods, 62(2), 373). However, very little is known about the functions of these metabolites in their natural habitat. In the Anjuna beach of Goa (west coast of India), they occur as dense mats and colonise a large intertidal area. The main focus of the present Invention^ therefore, is to ujidjijtjadj^e-^h^nucal antifouling defense properties against common micro-fouling organisms viz. bacteria and diatoms utilising the extract of Zoanthus sp and in turn for identifying a\natraJ product useful in antifouling technqlojgy.

Any surface exposed to marine environment undergoes sequential changes that begins with the adsorption of a layer of bio-polymers followed by the formation of a bacterial film, growth of pinnate diatoms and protozoans (Baier, 1984, in Marine Biodeterioration: An Interdisciplinary Study, J. D. Costlow and R. C. Tipper, ed, Naval Institute Press, Anapolis, Md., 57–62; Mitchell and Kirchman, 1984, in Marine Biodeterioration: An Interdisciplinary Study, J. D. Costlow and R. C. Tipper, ed, Naval Institute Press, Anapolis, Md., 49–56; Wahl, 1989, Mar. Ecol. Prog. Ser, 58, 175–189). Consequently, the variety of bacterial species forming the microbial film may influence, inhibit or at times have no effect upon the later settling species which constitute the invertebrate larvae that settle and metamorphose into adults (Bakus et al., 1986, J. Chem. Ecol, 12, 951–987). In most cases where it has been shown that a microbial film is necessary for settling of larvae and algal propagules, inhibition of bacterial growth would prevent the microbial film formation and in turn inhibit larval settlement, ultimately leaving the surfaces free of epibionts.

In this effort, the test animals were collected and the crude methanol extract was prepared. The antifouling potential of the extract was then explored against known fouling diatoms and bacteria in the laboratory. After testing the activity of the crude extract, it was fractionated using solvents of increasing polarity. These fractions were tested against the fouling diatoms. The results of the evaluation reveals that the extract of Zoanthus sp has the antifouling property.

OBJECTS OF THE PRESENT INVENTION

The main object of the present invention is to develop a composition comprising an extract from Zoanthus species.

Another main object of the present invention is to develop a composition having anti-fouling property.

Yet another object of the present invention is to develop fractions from extract of animal Zoanthus species.

Still another object of the present invention is to fractionate the crude extract using solvents of increasing polarity, viz; petroleum ether, chloroform, n-butanol and the aqueous fraction.

Still another object of the present invention is to identify the fraction which is most effective hi against fouling diatoms.

Still another object of the present invention is to develop a method of preparing composition comprising an extract from Zoanthus species.

Still another object of the present invention is to develop a method of preparing said composition having 100% anti-bacterial activity.

Still another object of the present invention is to develop a method of preparing said composition having 100% microbial growth inhibitory activity against fouling microbes.

Still another object of the present invention is to develop a method of preparing said composition with anti-microbial activity wherein, said activity is particularly effective in marine environment.

Still another object of the present invention is to develop a method of preparing said composition with anti-microbial activity wherein, said activity is particularly effective against bacteria and diatoms.

SUMMARY OF THE PRESENT INVENTION

The present invention relates to a composition useful as an anti-fouling agent by inhibiting microbial growth, said composition comprising extract and/or its fractions from Zoanthus sp. and optionally de-odorizing agents and a method of producing said extract and its fractions having about 100% anti-bacterial activity fouling microbes.

DETAILED DESCRIPTION OF THE PRESENT INVENTION

Accordingly, the present invention relates to a composition useful as an anti-fouling agent by inhibiting microbial growth, said composition comprising extract and/or its fractions from Zoanthus sp. and optionally de-odorizing agents and a method of producing said extract and its fractions having about 100% anti-bacterial activity fouling microbes.

In one embodiment of the present invention, a composition comprising extract and/or its fractions from Zoanthus sp, and optionally de-odorizing agents wherein said composition is useful as an anti-fouling agent against microbes.

In another embodiment of the present invention, wherein said extract and its fractions are prepared by using either polar or non-polar solvent.

In yet another embodiment of the present invention, wherein animal species preferably used for said activity is *Coelenterata Zoanthidea*.

In still another embodiment of the present invention, wherein said composition is prepared by using whole body tissue of said species.

In still another embodiment of the present invention, wherein said de-odorizing agent shows no affect on the activity of said extract and fractions.

In still another embodiment of the present invention, wherein ratio of said extract and/or fractions and de-odorizing agent is ranging between 1:1 to 1:10.

In still another embodiment of the present invention, wherein said composition is particularly effective against bacteria and diatoms.

In further embodiment of the present invention, a method of producing an extract and its fractions from Zoanthus sp, useful as an anti-fouling agent by inhibiting microbial growth.

In another embodiment of the present invention, soaking washed specimen of said species in methanol.

In yet another embodiment of the present invention, obtaining crude extract from the whole body tissue of said species.

In still another embodiment of the present invention, decanting the solvent extract.

In still another embodiment of the present invention, filtering decanted extract.

In still another embodiment of the present invention, evaporating the filtrate at 40° C. to obtain concentrate crude extract.

In still another embodiment of the present invention, fractionating concentrated crude extract using solvents of increasing polarity.

In still another embodiment of the present invention, introducing said crude extract at concentration ranging between 0.1 to 5.0-mg/6 mm-diameter disc in methanol on sterilized filter paper disc.

In still another embodiment of the present invention, evaporating the solvent from the disc.

In still another embodiment of the present invention, exposing microbes to said extract.

In still another embodiment of the present invention, laying said disc on agar plates seeded with test bacterium.

In still another embodiment of the present invention, running a control with solvent not containing extract.

In still another embodiment of the present invention, incubating said plates overnight for temperature ranging between 25 to 32° C.

In still another embodiment of the present invention, measuring growth inhibition zone.

In still another embodiment of the present invention, determining % inhibition of microbes using said extract.

In still another embodiment of the present invention, determining anti-diatomic activity of crude extract and said fractions separately, by placing diatoms with initial cell suspension of concentration ranging between 100 to 5000 cells/ml in flasks.

In still another embodiment of the present invention, adding said crude extract of concentration ranging between 10 to 5000 ppm to said cell suspension.

In still another embodiment of the present invention, adding said fractions of concentration ranging between 10 to 500 ppm in separate flasks.

In still another embodiment of the present invention, incubating flask at temperature ranging between 25 to 32° C. with 12 hrs light and next 12 hrs dark exposure conditions.

In still another embodiment of the present invention, determining % growth inhibition after about 6 days i.e., during exponential growth phase of diatoms.

In still another embodiment of the present invention, wherein said species preferably used for said activity is *Coelenterata Zoanthidea*.

In still another embodiment of the present invention, wherein said method is particularly effective in marine environment.

In still another embodiment of the present invention, wherein said method is particularly effective against bacteria and diatoms.

In still another embodiment of the present invention, wherein soaking said washed specimen in methanol for number of days ranging between 5–15.

In still another embodiment of the present invention, wherein said species is obtained from intertidal rocks.

In still another embodiment of the present invention, wherein decanted extract is filtered through whatman filter paper I.

In still another embodiment of the present invention, wherein filtrate is evaporated using vacuum.

In still another embodiment of the present invention, wherein said method uses zobell marine agar for bacterial culture.

In still another embodiment of the present invention, wherein concentration of said extract against bacteria is preferably about 0.5 mg/mm of diameter disc.

In still another embodiment of the present invention, wherein said extract is incubated at preferably 28° C.

In still another embodiment of the present invention, wherein growth inhibition zone less than 1 mm not been scored.

In still another embodiment of the present invention, wherein said fractionating solvents are selected from a group comprising petroleum ether, chloroform, n-butanol, and aqueous.

In still another embodiment of the present invention, wherein dissolving non-polar fraction petroleum ether in acetone (0.005–0.01 ml).

In still another embodiment of the present invention, wherein bacteria are selected from a group comprising *Bacillus cereus, B. circulans, Pseudomonas vesicularis*, and *P. putida*.

In still another embodiment of the present invention, wherein antibacterial activity of extract is 100%.

In still another embodiment of the present invention, wherein diatoms are selected from a group comprising *Navicula subinflata* and *Nitzschia closterium*.

In still another embodiment of the present invention, wherein calculating % growth inhibition with extract and/or fractions having more than 50% growth inhibition is considered as active ones.

In still another embodiment of the present invention, wherein said extract shows 100% inhibition in diatoms at concentration of 350 ppm and above.

In still another embodiment of the present invention, wherein all the said fractions of crude extract show inhibitory activity against diatoms.

In still another embodiment of the present invention, wherein petroleum ether fraction is most effective of all the fractions against diatoms.

In still another embodiment of the present invention, wherein petroleum ether fraction shows 100% inhibition at concentration of about 80 ppm and above against diatoms.

In still another embodiment of the present invention, wherein chloroform fraction shows about 100% inhibition in diatoms at concentration about 200 ppm.

In still another embodiment of the present invention, wherein n-butanol fraction shows about 100% inhibition against diatoms at concentration ranging between 150–250 ppm.

In still another embodiment of the present invention, wherein aqueous fraction shows inhibitory activity ranging between 70–85% against diatoms at concentration ranging between 140–250 ppm.

In still another embodiment of the present invention, wherein said extract/fractions do not have any toxic/adverse effect on non-target organisms.

In still another embodiment of the present invention, wherein assaying microbes in a culture media using agar plate diffusion method.

In still another embodiment of the present invention, wherein said method is used to prevent fouling in food articles.

In still another embodiment of the present invention, wherein said method is used to prevent fouling in biological specimens.

In further embodiment of the present invention, the present invention provides a process for the preparation of antifouling crude extract from Zoanthus sp and the said process comprising,
i) Collection of live/fresh specimens of Zoanthus sp from intertidal rocks.
ii) Washing the specimens clean with fresh sea water and soaking in methanol for
about 10 days iii) Filtering the extract through Whatman filter paper I and vacuum evaporating
at $40^U C$ to concentrate to crude residue. In an embodiment, the crude extract of Zoanthus sp is exhibiting antibacterial property.

In a preferred embodiment, the crude extract of Zoanthus sp is inhibiting growth of fouling bacteria such as *Bacillus cereus, Bacillus circulans, Bacillus pumilus, Pseudomonas vesiciulans* and *Pseudomonas putida*.

In another embodiment, the crude extract of Zoanthus sp is inhibiting growth of fouling diatoms at all concentrations.

In a preferred embodiment, the crude extract of Zoanthus sp is completely inhibiting growth of diatoms, *Navicula subinfiata* at and above 600 ppm concentration and *Nitzschia closterium* at and above 400 ppm concentration.

In still another embodiment of the present invention, a process for fractionating the crude antifouling extract from Zoanthus sp based on increasing polarity of the solvents, viz. petroleum ether, chloroform, n-butanol and aqueous fractions and testing the antifouling property of all these fractions against the fouling diatoms *Navicula subinflata* and *Nitzschia closterium*, the said process at comprising, obtaining crude extract from livefreshly collected Zoanthus sp, washing them clean with sea water, soaking in methanol for about 10 days, filtering the extract through Whatman filter paper I and concentrating to crude residue under vacuum at 40° C.

In an embodiment, the crude extract of Zoanthus sp is fractionated based on increasing polarity of solvents into petroleum ether, chloroform, n-butanol and aqueous fractions.

In another embodiment, all four fractions of the crude extract of Zoanthus sp are inhibiting the growth of fouling diatoms, *Navicula subinflata* and *Nitzschia closterium*.

In yet another embodiment, the percentage inhibition in all the fraction is varying with concentrations.

In still another embodiment, the petroleum ether fraction of the crude extract of Zoanthus sp is more effective in inhibiting growth of the fouling diatoms *Navicula subinflata* and *Nitzschia closteriwn*.

In one more embodiment, the petroleum ether fraction of the crude extract of Zoanthus sp completely inhibits growth of *Navicula subinflata* at and above 160 ppm and *Nitzschia closterium* at and above 80 ppm concentrations.

In further embodiment of the present invention, a process for the preparation of an antifouling crude extract from Zoanthus sp and testing the said crude extract on fouling bacteria and diatoms.

The invention also relates to a process for fractionation of the crude extract and testing the antifouling property of the fractions on fouling bacteria.

A process for the preparation of antifouling crude extract from Zoanthus sp and the said process comprising, Collection of live/fresh specimens of Zoanthus sp from intertidal rocks.

Washing the specimens clean with fresh seawater and soaking in methanol for about 10 days.

Filtering the extract through Whatman filter paper I and vacuum evaporating at 40° C. to concentrate to crude residue.

In still another embodiment of the present invention, wherein the crude extract of Zoanthus sp is exhibiting antibacterial property.

In still another embodiment of the present invention, wherein the crude extract of Zoanthus sp is inhibiting growth of fouling bacteria such as Bacillus cereus, Bacillus circulans, Bacillus pumilus, Pseudomonas vesiciularis and Pseudomonas putida.

In still another embodiment of the present invention, wherein the crude extract of Zoanthus sp is inhibiting growth of fouling diatoms at all concentrations.

In still another embodiment of the present invention, wherein the crude extract of Zoanthus sp is completely inhibiting growth of diatoms, Navicula subinflata at and above 600 ppm concentration and Nitzschia closterium at and above 400 ppm concentration.

In still another embodiment of the present invention, wherein-the crude extract of Zoanthus sp may have potential use as an antifouling agent/in aquatic environment.

In still another embodiment of the present invention, a process for fractionating the crude antifouling extract from Zoanthus sp based on increasing polarity of the solvents, viz. petroleum ether, chloroform, n-butanol and aqueous fractions and testing the antifouling property of all these fractions against fouling diatoms, the said process comprising, obtaining crude extract from live/freshly collected Zoanthus sp, washing them clean with sea water, soaking in methanol for about 10 days, filtering the extract through Whatman filter paper I and concentrating to crude residue under vacuum at 40° C.

In still another embodiment of the present invention, wherein the crude extract of Zoanthus sp is fractionated based on increasing polarity of solvents into petroleum ether, chloroform, n-butanol and aqueous fractions.

In still another embodiment of the present invention, wherein all the four fractions of the crude extract of Zoanthus sp are inhibiting the growth of fouling diatoms, Navicula subinflata and Nitzschia closterium.

In still another embodiment of the present invention, wherein the percentage inhibitions in all the fraction is varying with cone.

In still another embodiment of the present invention, wherein the petroleum ether fraction of the crude extract of Zoanthus sp is more effective in inhibiting growth of the fouling diatoms Navicula subinflata and Nitzschia closterium.

In still another embodiment of the present invention, wherein the petroleum ether fraction of the crude extract of Zoanthus sp completely inhibits growth of Navicula subinflata at and above 160 ppm and Nitzschia closterium at and above 80 ppm concentrations.

In still another embodiment of the present invention, wherein all fractions of the crude extract of Zoanthus Sp, more particularly the petroleum ether fraction may have potential use as an antifouling agent in the aquatic environment.

The invention is further explained with the help of the following examples and should not be construed to limit the scope of the invention.

EXAMPLE 1

Zoanthus sp collected from Anjuna beach (Goa) was used for the invention. The animals were carefully scrapped from the intertidal rocks during the low tide period using a metal spatula. About 2 kg wet weight of the specimens were used for the study. The specimens were thoroughly washed with fresh seawater and soaked in methanol for 6–10 days for crude extract preparation. Extracts were obtained from the whole body tissue. The solvent extract was decanted, filtered through Whatman filter paper I and vacuum evaporated at 40° C. to concentrate to crude extract. About 30 gm of crude extract was thus obtained. This example illustrates the methodology used for preparation of the crude methanol extract from Zoanthus sp.

EXAMPLE 2

Five bacterial isolates, all belonging to the fouling community were used for the assay. The bacterial assays were carried out by agar plate diffusion method (Amade et al., 1987, Mar. Biol, 94, 271–275) using Zobell marine agar (Himedia, Mumbai). Bacterial strains used for the assay were Bacillus cereus B. circulans. B. pumilus, Pseudomonas vesicularis and P. putida. Concentrations of 0.5-mg/6 mm-diameter disc of the extract prepared in methanol was introduced on sterilized filter paper discs. After solvent evaporation, the discs were laid on agar plates seeded with the test bacterium Controls (in duplicate) contained only the solvent. Four replicates of each concentration were used for the assay and average values are presented. Plates were incubated overnight at room temperature (<<28° C.). Growth inhibition zone was measured in mm. (Berquist and Bedford, 1978, Mar. Biol, 46, 215–221). Inhibition zones measuring <1 mm were not scored. The results of this activity is presented in Table 1. This example illustrates the methodology used for carrying out the antibacterial assay utilizing the extract of Zmanthus sp.

TABLE 1

Antibacterial screening with crude Zoanthus sp extract

| Bacteria | Inhibition |
| --- | --- |
| Bacillus cereus | + |
| Bacillus circulans | + |
| Bacillus pumilus | + |
| Pseudomonas vesicularis | + |
| Pseudomonas putida | + |

+ = 1–2 mm diameter inhibition

EXAMPLE 3

The diatoms, Navicula subinflata and Nitzschia closterium, both belonging to the fouling community, were maintained in enriched sea water (Gentile and Johnsor, 1974, in, Proceedings on a Workshop on Marine Bioassays, convened by Gerarldine Cox, USA, 128). Actively growing cultrs with an initial cell suspension of around 500–1000 cells ml$^{-1}$ were used for the assay. Concentration series of extract ranging between 200 and 1000 ppm. Aliquots of each extract stock solution (1 cc=50 mg) prepared in distilled water was taken corresponding to the desired experimental concentration and the volume was adjusted to 50 ml in 125 ml Erlenmeyer flasks. All assays were carried out in quadruplicate. Control flasks contained only the algae cells in medium. Flasks were incubated at room temperature (approx. 28° C.) with a 12 hr light and 12 hours dark exposure conditions. Growth inhibition was determined after 6 days i.e., during the exponential growth phase in terms of the number of attached algal cells using a Sedgwick rafter and is expressed as % growth inhibition in Table 2. Extracts that were able to produce 50% growth inhibition were considered as active ones. This example illustrates methodology used for carrying out the/antidiatom assay/utilizing the crude Zoanthus sp.

TABLE 2

Percentage growth inhibition of diatoms at different concentrations of the crude extract.of Zoanthus sp.

| Diatom species | Concentration (ppm) | % Inhibition +/− SD |
| --- | --- | --- |
| Navicula subinflata | 200 | 49.7 +/− .8 |
| | 400 | 96.3 +/− 0.4 |
| | 600 | 100.0 +/− 0.0 |
| | 800 | 100.0 +/− 0.0 |
| | 1000 | 100.0 +/− 0.0 |
| Nitzschia closterium | 200 | 5.5 ± 8.3 |
| | 400 | 100.0 +/− 0.0 |
| | 600 | 100.0 +/− 0.0 |
| | 800 | 100.0 ± 0.0 |
| | 1000 | 100.0 +/− 0.0 |

EXAMPLE 4

The crude extract was then fractionated into four fractions using solvents of increasing polarity viz. petroleum ether, chloroform, n-butanol and aqueous. All fractions were tested for the activity as shown in Table 3 using the method mentioned above. The non-polar fractions that were insoluble in distilled water during the preparation of. stock solution, were dissolved in acetone (0.005–0.01 ml). Control flasks for these sets contained sells plus acetone (equal volume added to make the stock solution) in the medium. This example illustrates the methodology used for fractionation of the crude extract and their testing for the anti-diatom assay.

TABLE 3

Percentage growth inhibition of diatoms at different concentrations of the four fractions of the crude extract of Zoanthus sp.

| | | % inhibition ± SD | | | |
| --- | --- | --- | --- | --- | --- |
| Diatom species | Concentration (ppm) | Petroleum ether | Chloroform | n-butanol | Aqueous |
| Navicula subinflata | 40 | 22.8 ± 3.0 | stimulation | 2.8 ± 1.6 | stimulation |
| | 80 | 30.5 +/− 3.0 | stimulation | 6.7 +/− 1.6 | 11.3 +/− 4.2 |
| | 120 | 99.7 +/− 0.1 | stimulation | 15.0 ± 1.2 | 42.2 +/− 9.3 |
| | 160 | 100.0 +/− 0.0 | 14.8 +/− 5.4 | 64.6 +/− 0.9 | 44.7 +/− 21.4 |
| | 200 | 100.0 +/− 0.0 | 89.4 +/− 11.7 | 74.5 ± 1.2 | 69.0 ± 7.1 |
| Nitzschia closterium | 40 | 81.0 ± 5.2 | stimulation | 5.2 ± 6.8 | 23.3 ± 11.3 |
| | 80 | 100.0 +/− 0.0 | 44.1 +/− 8.9 | 14.8 ± 1.6 | 30.7 +/− 3.0 |
| | 120 | 100.0 +/− 0.0 | 50.4 ± 5.9 | 59.9 ± 7.2 | 48.7 ± 13.7 |
| | 160 | 100.0 ± 0.0 | 77.7 +/− 14.8 | 100.0 +/− 0.0 | 67.2 +/− 6.3 |
| | 200 | 100.0 +/− 0.0 | 100.0 ± 0.0 | 100.0 ± 0.0 | 77.8 ± 8.7 |

EXAMPLE 5

This example illustrates the methodology used for the treatment of results in the antidiatom assay using crude extract and of Zoanthus sp.

The percentage growth inhibition was calculated using the formula, $$\frac{(A-O)-(B-O)}{(A-O)} \times 100$$

Where, O=inoculum cell numbers at zero hours

A=attached cell numbers in control flask after 6 days

B=attached cell numbers in experimental flask after 6 days

Advantages of the Present Invention:

1. This is for the first time that the antifouling property of the crude extract of Zoanthus sp has been identified.
2. Laboratory studies indicated that the crude extract of Zoanthus sp was effectively inhibiting growth of fouling bacteria and diatoms which are the primary organisms to colonize any marine substratum.
3. All the four fractions, viz. petroleum ether, chloroform, n-butanol and aqueous fractions separated from the crude extract exhibited antifouling property.
4. Among the four fractions, the petroleum ether fraction was found to be more effective in inhibiting the growth of fouling diatoms.
5. This being a natural product may not have any toxic/adverse effects on non-target Organisms.
6. This has the potential to form a natural compound in antifouling products.

What is claimed is:

1. A method of producing an extract and its fractions from Zoanthus sp, useful as an anti-fouling agent by inhibiting microbial growth, said method comprising:
   (a) soaking washed specimen of said species in methanol,
   (b) obtaining crude extract from the whole body tissue of said species as a solvent extract, (c) decanting the solvent extract to obtain a decanted extract, (d) filtering the decanted extract to obtain a filtrate, (e) evaporating the filtrate at 40° C. to obtain a concentrated crude extract, fractionating the concentrated crude extract using solvents of increasing polarity.

2. A method as claimed in claim 1, wherein said washed specimen is soaked in methanol for a number of days ranging between 5–15.

3. A method as claimed in claim 1, wherein said species is obtained from intertidal rocks.

4. A method as claimed in claim 1, wherein the decanted extract is filtered through Whatman filter paper I.

5. A method as claimed in claim 1, wherein the filtrate is evaporated using a vacuum.

6. A method as claimed in claim 1, wherein said solvents of increasing polarity are selected from the group consisting of petroleum ether, chloroform, n-butanol, and aqueous.

7. A method as claimed in claim 1, wherein a non-polar fraction petroleum ether is dissolved in 0.005–0.01 ml acetone.

8. A method as claimed in claim 1, wherein said extract shows 100% inhibition in diatoms at concentration of 350 ppm and above.

9. A method as claimed in claim 1, wherein all said fractions of crude extract show inhibitory activity against diatoms.

10. A method as claimed in claim 1, wherein a petroleum ether fraction is effective against diatoms.

11. A method as claimed in claim 1, wherein a petroleum ether raction shows 100% inhibition at concentration of about 80 ppm and above against diatoms.

12. A method as claimed in claim 1, wherein a chloroform fraction shows about 100% inhibition against diatoms at a concentration of about 200 ppm.

13. A method as claimed in claim 1, wherein an n-butanol fraction shows about 100% inhibition against diatoms at a concentration ranging from between 150–250 ppm.

14. A method as claimed in claim 1, wherein an aqueous fraction shows inhibitory activity ranging between 70–85% against diatoms at concentration ranging between 140–250 ppm.

15. A method as claimed in claim 1, wherein said extract and said fractions do not have any toxic or adverse effect on non-target organisms.

\* \* \* \* \*